United States Patent [19] [11] 4,420,306
Orlowski et al. [45] Dec. 13, 1983

[54] TETRAACRYLIC AND TETRAMETHACRYLIC ESTERS AND DENTAL MATERIALS CONTAINING SAME

[75] Inventors: Jan A. Orlowski, Altadena, Calif.; Helmar Wagner, Darmstadt-Arheilgen, Fed. Rep. of Germany; David V. Butler, W. Covina, Calif.

[73] Assignee: Blendax-Werke R. Schneider GmbH & Co., Mainz, Fed. Rep. of Germany

[21] Appl. No.: 391,922

[22] Filed: Jun. 24, 1982

[51] Int. Cl.$^3$ .............................................. A61K 6/08
[52] U.S. Cl. ..................................... 433/228; 106/35; 260/998.11; 433/199; 433/201; 433/202; 523/115; 523/116; 523/117; 560/25; 560/115; 560/158
[58] Field of Search ............... 433/199, 201, 202, 212, 433/226, 228; 560/25, 115, 158; 106/35; 260/998.11; 523/116, 117

[56] References Cited

U.S. PATENT DOCUMENTS

| 3,425,988 | 2/1969 | Gorman et al. | 260/47 |
| 3,629,187 | 12/1971 | Waller | 260/41 R |
| 3,801,344 | 4/1974 | Dietz | 106/300 |
| 3,808,170 | 4/1974 | Rogers | 260/42.53 |
| 4,347,174 | 8/1982 | Nagase et al. | 523/116 |
| 4,383,826 | 5/1983 | Butler et al. | 433/228 |

FOREIGN PATENT DOCUMENTS 2079297 1/1982 United Kingdom .

Primary Examiner—Lorenzo B. Hayes
Attorney, Agent, or Firm—Connolly and Hutz

[57] ABSTRACT

Tetraacrylic acid and tetramethacrylic acid esters and dental restorative and filling materials containing the esters.

12 Claims, No Drawings

TETRAACRYLIC AND TETRAMETHACRYLIC ESTERS AND DENTAL MATERIALS CONTAINING SAME

Our invention is related to new, polymerizable tetra(meth)acrylic compounds and their use in binding agents, especially dental materials as well as a dental restoring and filling material.

There are existing numerous polymerizable compounds having more than one double bond in the molecule. These compounds are used for various purposes, especially as binding agents for the preparation of different adhesives, a.o. in medicine and dentistry, for the preparation of dental cements, dental restoring and filling materials, dental sealing materials, orthopedic and orthodontic adhesives, etc..

We have now found that a new class of monomers being prepared by reaction of aliphatic, aromatic or cycloaliphatic diisocyanates with certain hydroxyl groups bearing di(meth)acrylates are especially suitable as binding agents and adhesives, especially in the above mentioned areas.

Thus, object of our invention are new compounds of the general formula

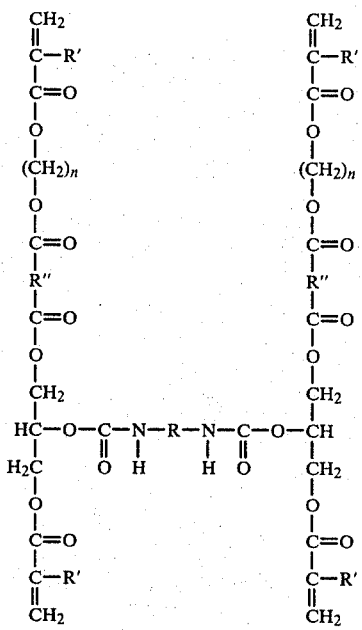

where R is a divalent (ar)aliphatic, cycloaliphatic, or aromatic group with 4 to 18 carbon atoms, R' is H or a methyl group, R" is a —CH=CH—, —CH$_2$CH$_2$—, —CH$_2$CH$_2$CH$_2$—, —CH$_2$CH$_2$CH$_2$CH$_2$—, optionally substituted or hydrogenated benzene group, or a cyclohexane, cyclohexene, or a cisnorbornene group, and n is 2 or 3.

The residue R especially means a tetra- or hexamethylene group, a phenylene, a toluylene, a methylenebisphenyl, a propylenbisphenyl, a cyclohexane, or a methylenebiscyclohexyl, or a propylenebiscyclohexyl group.

R' is a hydrogen atom or a methyl group; the methacrylic compound is preferred.

R" especially stands for a —CH=CH— group (derived from maleic acid), a benzene group (derived from phthalic acid), a tetrahydrobenzene group (derived from 4-cyclohexene 1,2-dicarboxylic acid), a cyclohexane group (derived from cyclohexane 1,2-dicarboxylic acid), or a cis-norbornene group (derived from cis-norbornene dicarboxylic acid), however, e.g. also malonic acid, succinic acid, glutaric acid, and adipic acid compounds are suitable.

The preparation of the polymerizable compounds with 4 (meth)acrylic groups according to our invention may be effected by the following procedure:

An anhydride of an aliphatic, cycloaliphatic or aromatic dicarboxylic acid is esterified with hydroxyethyl or hydroxypropyl acrylate or the corresponding methacrylate, preferably at temperatures between about 120° to about 170° C.

Then this (meth)acrylic monoester is reacted with glycidyl acrylate or glycidyl methacrylate to the corresponding 2-(meth)acroylethyl, 3-(meth)acroyl 2-hydroxypropyl ester, or 3-(meth)acroylpropyl, 3-(meth)acroyl 2-hydroxypropyl ester.

This intermediate product is reacted with a diisocyanate at about 40° to about 100° C. to give the corresponding biscarbamate.

From the German Published Patent Nos. 2,357,324 and 2,419,887, and the U.S. Pat. No. 3,425,988 (meth)acrylic esters having carbamic acid groups in the molecule are well known. However, these known products are different in structure and properties from the monomers according to the invention and therefore do not show the advantages which may be realized by use of the compositions according to our invention.

Moreover, British Published Patent Specification No. 2,079,297 discloses a curable dental filling material containing as resin components reaction products from diisocyanates and hydroxyalkyl diacrylates and dimethacrylates of the general formula

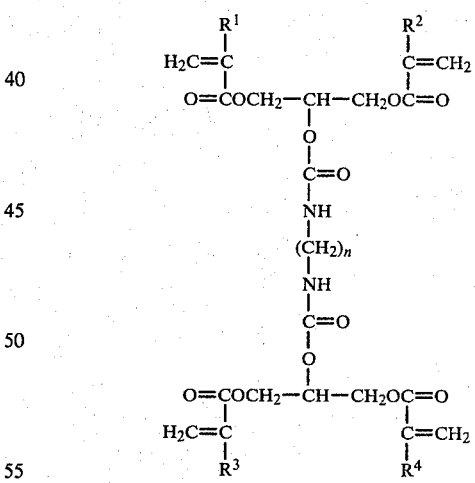

where R$^1$, R$^2$, R$^3$ and R$^4$ are hydrogen or a methyl group, and n is a number from 2 to 10.

However, the improvement of the properties of the cured dental filling materials containing such monomers does not meet the requirements of the dental practice, especially as relates to mechanical properties, particularly the hardness.

The products according to our invention are principially suitable for all those uses where monomers with more than one polymerizable double bond in the molecule are used. As previously indicated, they are especially suitable for use in medicine and denistry.

In the last years, in denistry the so-called "composites" have got increasing importance, as these products are easily and safely to apply by the dentist and are tolerated well by the patients. They are approaching the aim to remove the amalgam filling materials being criticized for physiological reasons.

These composites usually are composed of inorganic filling materials and polymerizable compounds.

Disadvantages of composites compared with conventional filling materials are their susceptibility to abrasion and shrinkage and their water-absorption. Secondary caries may be the result caused by the possible shrinkage between the border of the cavity and the filling in the tooth.

Therefore, those skilled in the art have made serious attempts to prepare composites having no or at least a low degree of shrinkage, a low water sorption, good mechanical properties, especially as relates to hardness, and are color-stable.

These properties may be performed by a high percentage of inorganic filling material in the filling compositions. However, the maximum filler portion is related to the properties of the monomers being present in the composition.

Conventional composites being on the market generally have the following mechanical properties after curing.

| | |
|---|---|
| Water absorption at 37° C. | 0,7–1,2 mg/cm$^{2(x)}$ |
| Compressive strength | 30.000 to 40.000 psi |
| Diametral tensile strength | 3.480 to 4.200 psi$^{(x)}$ |
| Hardness (Barcol) | 98 |
| Color stability | No discoloration detectable$^{(x)}$ |

$^{(x)}$Determined according to ADA Specification No. 27 (Journal of the American Dental Association, Vol. 94 (June 1977)).

We have now found that these above referred mechanical properties of conventional, well-known composites may be considerably improved by use of the new monomers according to our invention which is probably caused by a considerably increase of the ratio of inorganic filler content to resin. This causes an improvement of the physical properties of the cured fillings, especially as regards to hardness and abrasion resistance.

The filler content in the filling compositions according to the invention may be increased until up to about 90%.

Therefore it is an object of our invention to prepare a dental filling material being characterized by a portion of at least one of the new monomers according to the invention, at least one inorganic filler, a polymerization initiator or accelerator as well as optionally further compounds being well-known in those compositions such as other monomers, UV-absorbers, stabilizers, colors and dyes, etc.

The used inorganic fillers may be X-ray transparent or X-ray opaque. Suitable examples are the different silicas such as glass (pulverized glass), quartz, borosilicate glass, and other glasses like quantzite, cristobalite, etc. Suitable X-ray opaque fillers are bariumaluminium silicate, lithiumaluminium silicate, or glass ceramic fillers containing, e.g., the elements lanthanum or zirconium. Suitable X-ray opaque fillers are for example, disclosed in U.S. Pat. Nos. 3,801,344, 3,808,170 and 9,975,203 as well as in German Published Patent No. 2,347,591.

To improve the compatibility of the inorganic filling material with the organic monomers the fillers may be silanized as well known in the art.

The particle diameters of the inorganic fillers are normally between at about 0,01 and 100 microns. In many cases it is possible and also suitable to use combinations of fillers with high and low particle diameters, whereby the preferred particle diameter is between about 0.05 and about 50, especially about 30 microns.

Suitable fillers are also described in our co-pending applications, Ser. No. 304,647, of Sept. 23, 1981, and Ser. No. 368,743, of Apr. 15, 1982.

In principle, composites are used in two modifications, either as two-phase compositions or as one-phase compositions.

In the two-phase compositions, one phase is containing a polymerization initiator, e.g. a peroxide, and the other phase contains an accelerator, e.g. an organic amine. Both phases are brought together shortly before the filling of the tooth is effected; the polymerization (curing) is carried out in the open cavity fitted with a bonding or reliner material, resp.

One-phase preparations are polymerizing under the influence of light, for example UV or laser light, and contain a photopolymerization initiator and optionally an accelerator therefore.

Of course, the use of the new monomers according to the invention is possible in both, two-phase and one-phase preparations.

As mentioned, one-phase preparations are polymerized by the influence of light. Suitable photopolymerization initiators are well-known: Preferred compounds for this purpose are carbonyl compounds, especially benzil and benzil derivatives like 4,4-oxidibenzil or other dicarbonyl compounds, e.g. diacetyl, 2,3-pentandione, or metal carbonyls, quinones and their derivatives. The proportion of photopolymerization initiators in the whole composition is from about 0,01 to about 5% by weight.

These one-phase preparations preferably contain also so-called polymerization accelerators. These are substances which accelerate the polymerization reaction in the presence of polymerization initiators.

Well-known accelerators are, for example, different amines such as p-toluidine, dimethyl p-toluidine, trialkyl amines, polyamines like N,N,N',N'-tetraalkyl alkylenediamines and sulfimides, preferably in an amount from about 0,01 to about 5% of the whole composition.

If the dental restoring material containing the new monomers according to the invention shall not be light-curable and be present in two phases being separated until their application, one of these mixtures contains a polymerization initiator.

These are preferably peroxides forming radicals when initiating the polymerization of the unsaturated compounds. Usual peroxides are, for example, aryl peroxides like benzoyl peroxide, cumene hydroperoxide, urea peroxide, tert.-butyl hydroperoxide, or perbenzoates and silyl peroxides, preferably in an amount of 0,01 to about 5, especially about 0,5 to about 2,5% by weight of the whole composition.

If one phase of the two-phase material contains a polymerization initiator it is suitable to add an accelerator of the above described type, preferably an amine, to the other phase.

In the dental restoring materials containing the new monomers of our invention polymerizable organosilicon compounds may be used, such as methacroyl alkyl trihydroxysilanes or methacroyl trimethoxysilane, to improve the adhesion between inorganic filler and resin.

In addition to the new monomers according to the invention other monomers already proposed for this purpose may be used in dental restoring materials. Such monomers are, for example, alkandiol dimethacrylates like 1,6-hexandiol dimethacrylate, 1,4-butandiol dimethacrylate, or tri- or tetraethylenglycol dimethacrylate, bis-(2-methacroylethyl) phthalate, isophthalate or terephthalate, trimethylolpropane di- and trimethacrylate, reaction products from diisocyanates and simple hydroxyalkyl methacrylates as described, e.g., in German Published patent application No. 2,312,559, reaction products from bisphenols, particularly Bisphenol A, and glycidyl methacrylate (Bis-GMA), adducts from (di)isocyanates and 2,2-propane bis-3-(4-phenoxy)-1,2-hydroxypropane-1-methacrylate according to U.S. Pat. No. 3,629,187, and other suitable polymerizable compounds already disclosed for this purpose.

Suitable monomers are also the adducts from methacroylalkyl ethers, alkoxybenzenes and alkoxycycloalkanes, resp., and diisocyanates disclosed in European Published patent application No. 44,352.

Composite materials may contain low amounts of suitable dyestuffs to adjust the color of the fillings as natural as possible.

It may be also useful to include low amounts of UV stabilizers, for example hydroquinone, p-benzoquinone, tert.-butyl hydroxytoluene, etc.

The following examples will illustrate our invention:

EXAMPLE A (a) 98 g maleic anhydride and 0,35 g 2,5-di-tert.-butyl-4-methyl phenol are dissolved in 130 g hydroxyethyl methacrylate at 70° C. under stirring on a reflux condenser. Then, the temperature of the mixture is increased to 130° C. and 180 g glycidyl methacrylate are added stepwise under stirring at 130°–140° C. during one hour. All 30 minutes acid number and epoxy equivalent value are determined. When the acid number falls below 0,5, the condenser is removed from the reaction vessel, and air is bubbled through the reaction mixture until the epoxy equivalent value reaches 10,000. The reaction is finished after about 5 hours; 2-methacroylethyl, 3-methacroyl 2-hydroxypropyl(maleate)

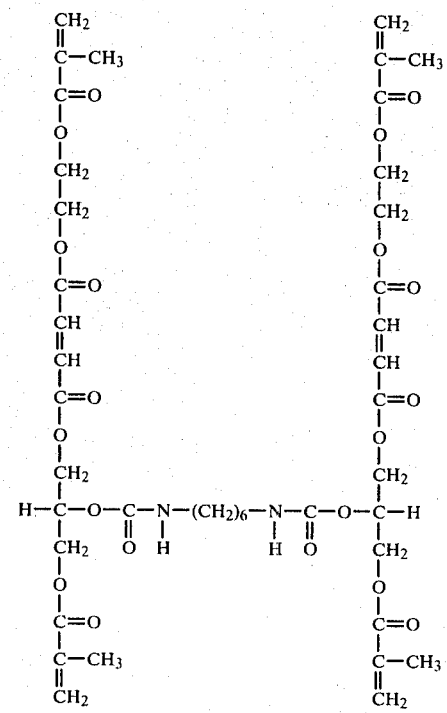

Refraction index (100° C.): 1,470.

In the same way the corresponding tetramethylene and phenylene biscarbamates are prepared.

EXAMPLE B 185 g of the 2-methacroylethyl, 3-methacroyl-2-hydroxypropyl (maleate) prepared according to example A (a) are stirred together with 60 g bis(4-isocyanatophenyl)methane at 90°–95° C.

The reaction is finished after about 90 minutes when no free isocyanate groups are detectable.

The reaction product is a viscous colorless liquid which contains methylenebisphenyl carbamate of 2-methacroylethyl, 3-methacroyl-2-hydroxy propyl(maleate) with the following structure:

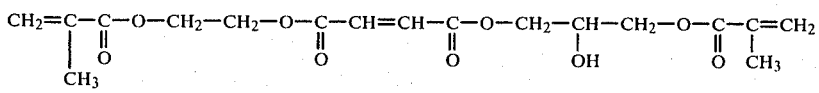

is obtained in practically quantitative yield.

Corresponding acrylic compounds are prepared in an analogous way.

(b) 92,5 g of the reaction product prepared according to (a) and 20 g hexamethylene diisocyanate are stirred together at 70° C. in presence of 0,1 g dibutyl stannodiacetate. The reaction is finished after about 3 hours when no free isocyanate groups are detectable.

The reaction product, a colorless viscous liquid, has the following structure:

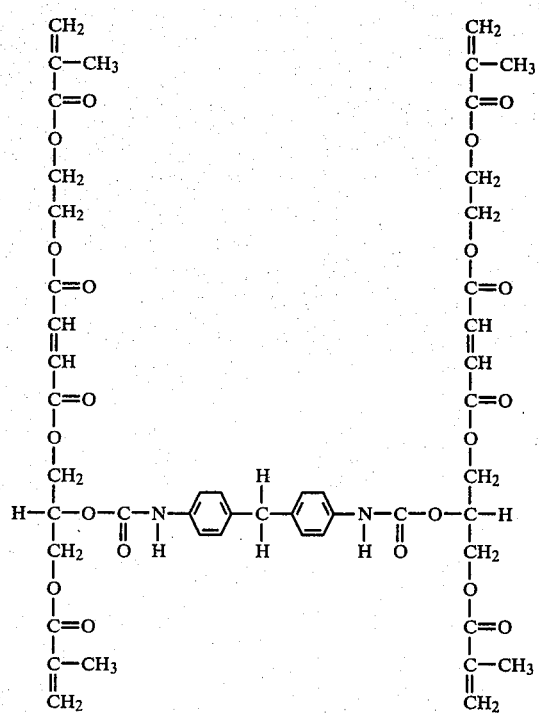

Refraction index (100° C.): 1,513.

In the same way the corresponding methylenebiscyclohexyl carbamate is prepared.

EXAMPLE C (a) 222 g phthalic anhydride and 0,3 g 2,6-di-tert.-butyl-4-methyl phenol are dissolved under stirring in 195 g 2-hydroxyethyl methacrylate. The temperature is increased to 135° C. at the condenser and 270 g glycidyl methacrylate are added stepwise under stirring at 135°–145° C. during one hour. All 30 minutes acid number and epoxy equivalent value are determined. After further stirring of 2,5 hours, the acid number is 0,2 and the epoxy equivalent value is 5,000. The condenser is removed, and the excess of glycidyl methacrylate which has not reacted is removed with air until the epoxy equivalent value reaches 10,000.

2-methacroylethyl, 3-methacroyl 2-hydroxypropyl (phthalate) with the structure

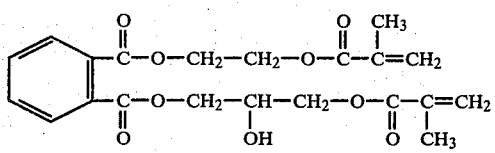

is obtained in practically quantitative yield.

(b) 211 g of the reaction product prepared according to (a) and 90 g hexamethylene diisocyanate are stirred together at 70° C. in presence of 0,25 g dibutyl stannodiacetate. The reaction is finished after about 5 hours when no free isocyanate groups are detectable.

The reaction product, a colorless viscous liquid was identified as hexamethylene biscarbamate of 2-methacroylethyl, 3-methacroyl-2-hydroxy propyl(phthalate) with the following structure

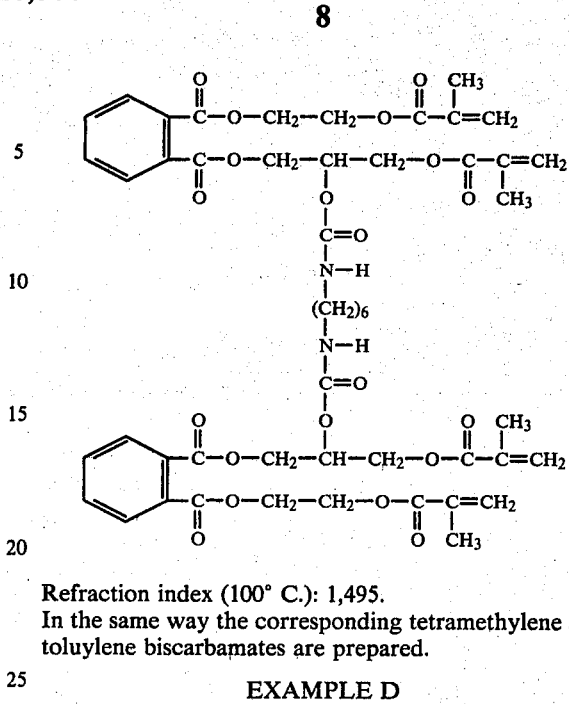

Refraction index (100° C.): 1,495.

In the same way the corresponding tetramethylene and toluylene biscarbamates are prepared.

EXAMPLE D

Methylenebisphenyl carbamate of 2-methacroylethyl, 3-methacroyl-2-hydroxy propyl(phthalate) is obtained corresponding to the conditions described in example C (b):

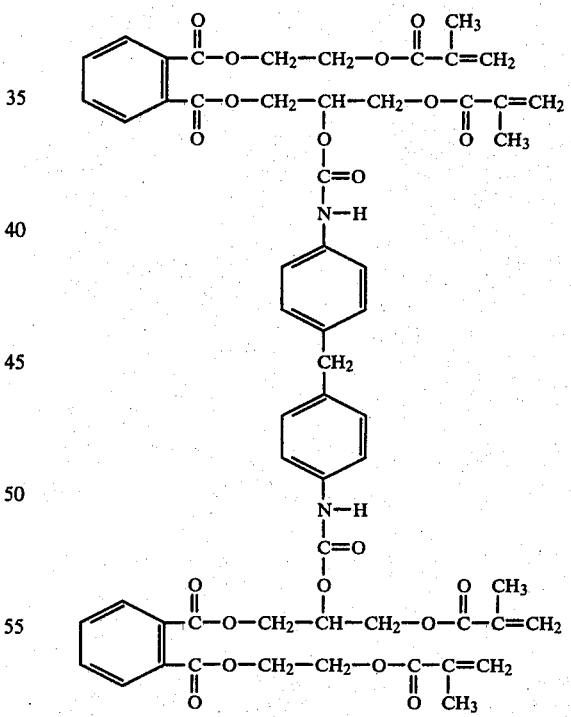

Refraction index (100° C.): 1,495.

In the same way the methylene biscyclohexyl carbamate is prepared.

EXAMPLE E (a) According to the procedure described in example C, from hydroxyethyl methacrylate and cyclohexane-1,2-dicarboxylic anhydride, and following reaction with glycidyl methacrylate the 2-methacroylethyl, 3- methacroyl-2-hydroxypropyl ester of 1,2-cyclohexane carboxylic acid

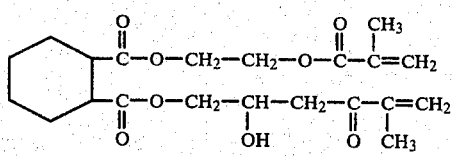

is prepared.

(b) The reaction product prepared according to (a) is converted to the hexamethylene biscarbamate of the formula

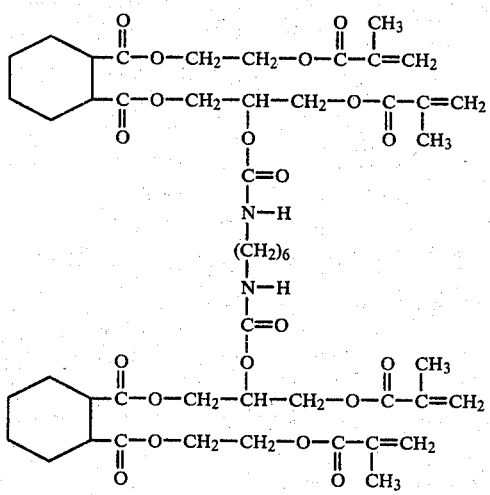

as described in the foregoing examples with 1,6-hexamethylene diisocyanate.

The corresponding 1,4-tetramethylene biscarbamates and methylenebisphenyl and -biscyclohexyl carbamates are prepared analogously.

The corresponding acrylic acid derivatives are prepared in the same way.

The following examples prove the superior properties of dental restoring materials prepared by the use of the monomers according to the invention.

EXAMPLE 1

|  | (parts by weight) | |
|---|---|---|
|  | Part A | Part B |
| 2,2-bis[4'(2''-methacroylethyloxy) phenyl]propane | 56 | 56 |
| 2,2-bis[4'(3''-methacroyl-2''-hydroxy-propoxy)phenyl]propane | 10 | 10 |
| Triethyleneglycol dimethacrylate | 19 | 19 |
| Hexamethylene biscarbamate of 2-methacroyl-, 3-methacroyl-2-hydroxypropyl(phthalate) | 15 | 15 |
| Hydrophobized barium borosilicate glass (Average particle size ~10 microns) | 600 | 600 |
| Hydrophobized silica (Average particle size ~25-50 millimicrons) | 40 | 40 |
| Bis(tert.-butyl)p-hydroxy toluene | 0,03 | 0,12 |
| 2-hydroxy-4-methoxy benzophenone | 0,6 | 0,6 |
| Benzoyl peroxide |  | 2 |
| N,N—bis(diethanolo)-p-toluidine | 4 |  |

For curing equal amounts of A and B were mixed and polymerized at 23° C. for 150 seconds.

The resulting polymer showed the following properties:

| Translucency factor ($C_{70}$) | 0,4 |
|---|---|
| Diametral tensile strength | 7.500 psi |
| Water sorption | 0,42 mg/cm$^2$ |
| Hardness (Barcol) | 98 |

EXAMPLE 2

|  | (parts by weight) | |
|---|---|---|
|  | Part A | Part B |
| 2,2-bis[4'(2''-methacroylethyloxy) phenyl]propane | 56 | 56 |
| 2,2-bis[4'(3''-methacroyl-2''-hydroxy-propoxy)phenyl]propane | 10 | 10 |
| Triethyleneglycol dimethacrylate | 19 | 19 |
| 2-hydroxy-4-methoxy benzophenone | 0,6 | 0,6 |
| Bis(tert.-butyl)p-hydroxy toluene | 0,03 | 0,12 |
| N,N—bis(diethanolo)-p-toluidine | 4 |  |
| Benzoyl peroxide |  | 2 |
| Hexamethylene biscarbamate of 2-methacroylethyl-, 3-methacroyl-2-hydroxypropyl(maleate) | 15 | 15 |
| Hydrophobized barium borosilicate glass (Average particle size ~10 microns) | 600 | 600 |
| Hydrophobized silica (Average particle size ~25-50 millimicrons) | 40 | 40 |

For curing equal amounts of A and B were mixed and polymerized at 23° C. for 150 seconds.

The resulting polymer showed the following properties:

| Translucency factor ($C_{70}$) | 0,4 |
|---|---|
| Diametral tensile strength | 5.700 psi |
| Water sorption | 0,59 mg/cm$^2$ |
| Hardness (Barcol) | 97 |

EXAMPLE 3

|  | (parts by weight) | |
|---|---|---|
|  | Part A | Part B |
| 2,2-bis[4'(2''-methacroylethyloxy) phenyl]propane | 56 | 56 |
| 2,2-bis[4'(3''-methacroyl-2''-hydroxy-propoxy)phenyl]propane | 10 | 10 |
| Triethyleneglycol dimethacrylate | 19 | 19 |
| 2-hydroxy-4-methoxy benzophenone | 0,6 | 0,6 |
| Bis(tert.-butyl)p-hydroxy toluene | 0,03 | 0,12 |
| N,N—bis(diethanolo)-p-toluidine | 4 |  |
| Benzoyl peroxide |  | 2 |
| Hexamethylene biscarbamate of 2-methacroylethyl-, 3-methacroyl-2-hydroxypropyl ester of cyclohexane-1,2-dicarboxylic acid | 15 | 15 |
| Hydrophobized barium borosilicate glass (Average particle size ~5-15 microns) | 600 | 600 |
| Hydrophobized silica (Average particle size ~20-50 millimicrons) | 40 | 40 |

For curing equal amounts of A and B were mixed and polymerized at 23° C. for 150 seconds.

The resulting polymer showed the following properties:

| Translucency factor ($C_{70}$) | 0,4 |
|---|---|
| Diametral tensile strength | 6.200 psi |
| Water sorption | 0,42 mg/cm$^2$ |
| Hardness (Barcol) | 98 |

EXAMPLE 4

|  | (parts by weight) | |
|---|---|---|
|  | Part A | Part B |
| 2,2-bis[4'(2''-methacroylethyloxy) phenyl]propane | — | 56 |
| 2,2-bis[4'(3''-methacroyl-2''-hydroxy-propoxy)phenyl]propane | — | 10 |
| Triethyleneglycol dimethacrylate | 20 | 19 |
| Methylenebisphenyl carbamate of 2-methacroylethyl-, 3-methacroyl-2-hydroxypropyl(tetrahydrophthalate) | 80 | 15 |
| 2-hydroxy-4-methoxybenzophenone | 0,5 | 0,5 |
| Bis(tert.-butyl)-p-hydroxytoluene | 0,03 | 0,12 |
| N,N—bis(diethanolo)-p-toluidine | 4 |  |
| Benzoyl peroxide |  | 2,2 |
| Hydrophobized barium borosilicate glass (Average particle size ~5-15 microns) | 600 | 600 |
| Hydrophobized silica (Average particle size ~25-50 millimicrons) | 40 | 40 |

For curing equal amounts of A and B were mixed and polymerized at 23° C. for 150 seconds.

The resulting polymer showed the following properties:

| Translucency factor ($C_{70}$) | 0,45 |
|---|---|
| Diametral tensile strength | 8.200 psi |
| Water sorption | 0,65 mg/cm$^2$ |
| Hardness (Barcol) | 98 |

In the following an example for a UV hardening dental laquer is given:

| Hexamethylene biscarbamate of 2-methacroyl-ethyl, 3-methacroyl 2-hydroxypropyl ester of cis-norbornene dicarboxylic acid (bicyclo 2.2.1.-hept-2-en-2,3-dicarboxylic acid) | 12,0% by weight |
|---|---|
| 2-Ethylhexyl methacrylate | 23,0% by weight |
| Ethyleneglycol dimethacrylate | 25,0% by weight |
| 1,6-Hexandiol dimethacrylate | 28,3% by weight |
| Acetophenone | 0,7% by weight |
| N,N—Di(2-hydroxyethyl)p-toluidine | 1,0% by weight |

We claim:
1. Tetraacrylic and tetramethacrylic acid esters of the general formula

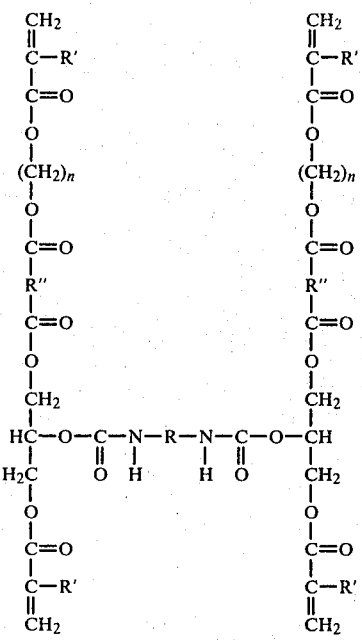

where R is a divalent (ar)aliphatic, cycloaliphatic, or aromatic group with 4 to 18 carbon atoms; R' is H or methyl; R'' is a —CH=CH—, —CH$_2$CH$_2$—, —CH$_2$CH$_2$CH$_2$—, —CH$_2$CH$_2$CH$_2$CH$_2$—, an optionally substituted or hydrogenated benzene group, a cyclohexane group, or a cis-norbornene group, and n is 2 or 3.

2. Compounds according to the general formula of claim 1, where R is a hexamethylene group.

3. Compounds according to the formula of claim 1, where R is a phenylene or toluylene group.

4. Compounds according to the formula of claim 1, where R is a methylene biscyclohexyl group.

5. Compounds according to the formula of claim 1, where R is a methylene bisphenyl group.

6. Compounds according to the formula of claim 1, where R is a tetramethylene group.

7. Compounds according to the formula of one of the claims 1 to 6, where R'' is a —CH=CH— group.

8. Compounds according to the formula of one of the claims 1 to 6, where R'' is a benzene group.

9. Compounds according to the formula of one of the claims 1 to 6, where R'' is a tetrahydrobenzene group.

10. Compounds according to the formula of one of the claims 1 to 6, where R'' is a cyclohexane group.

11. Dental restorative and filling material containing at least one inorganic filler, at least one polymerization initiator, at least one polymerization accelerator, and at least one of the compounds according to one of the claims 1 to 6.

12. Dental restorative and filling material according to claim 11, containing the following components:
5 to 50% by weight of at least one of said compounds;
0,1 bis 5,0% by weight of at least one polymerization initiator and/or polymerization accelerator and
50 to 90% by weight of at least one filler.

* * * * *